US011679237B2

(12) United States Patent
Scheltes et al.

(10) Patent No.: US 11,679,237 B2
(45) Date of Patent: Jun. 20, 2023

(54) MEDICAL DEVICE WITH FLEXIBLE TIP

(71) Applicant: DEAM HOLDING B.V., Groningen (NL)

(72) Inventors: Julien Serge Scheltes, Amsterdam (NL); Wimold Pieter Steven Peters, Amsterdam (NL)

(73) Assignee: DEAM HOLDING B.V., Groningen (NL)

( * ) Notice: Subject to any disclaimer, the term of this patent is extended or adjusted under 35 U.S.C. 154(b) by 433 days.

(21) Appl. No.: 16/627,543

(22) PCT Filed: Jun. 27, 2018

(86) PCT No.: PCT/NL2018/050414
§ 371 (c)(1),
(2) Date: Dec. 30, 2019

(87) PCT Pub. No.: WO2019/004826
PCT Pub. Date: Jan. 3, 2019

(65) Prior Publication Data
US 2020/0179651 A1    Jun. 11, 2020

(30) Foreign Application Priority Data
Jun. 29, 2017    (NL) ...................................... 2019146

(51) Int. Cl.
*A61M 25/01*    (2006.01)
(52) U.S. Cl.
CPC .... *A61M 25/0147* (2013.01); *A61M 25/0136* (2013.01); *A61M 2205/103* (2013.01)
(58) Field of Classification Search
CPC ........... A61B 2017/00398; A61B 2017/00327; A61B 2017/00318; A61M 25/0136; A61M 25/0147
See application file for complete search history.

(56) References Cited

U.S. PATENT DOCUMENTS 3,572,325 A    3/1971  Bazell et al.
3,605,725 A *  9/1971  Bentov ................ A61B 1/0052
                                        604/95.04
(Continued)

FOREIGN PATENT DOCUMENTS

CN    106217345 A  * 12/2016  ............. A61B 1/005
CN    106562806 A  *  4/2017  ....... A61B 17/00234
(Continued)

OTHER PUBLICATIONS

International Search Report, PCT/NL2018/050414, dated Sep. 21, 2018.

*Primary Examiner* — Katherine H Schwiker
*Assistant Examiner* — Adam J. Cermak
(74) *Attorney, Agent, or Firm* — Nixon & Vanderhye

(57) ABSTRACT

A medical device includes a handle; flexible tubing extending from the handle and having a proximal end fixed to the handle; flexible tip attached to the distal end of the flexible tubing; a tip actuator assembly adjusting the bending plane of the tip relative to the distal end and adjusting the degree of bending of the tip in the bending plane; user operable controls on the handle and moveable in a first, rotational direction relative to the handle and to a tip actuator assembly around an axis causing the tip actuator assembly to adjust the bending plane of the tip substantially and moveable relative to the handle and the tip actuator assembly along a second, substantially linear direction towards and away from the proximal end of the flexible tubing, causing the tip actuator assembly to adjust bending of the tip in the bending plane without adjusting the bending plane.

11 Claims, 15 Drawing Sheets

(56) References Cited

U.S. PATENT DOCUMENTS

| | | | |
|---|---|---|---|
| 5,195,968 A | 3/1993 | Lundquist et al. | |
| 5,334,168 A | 8/1994 | Hemmer | |
| 5,358,479 A | 10/1994 | Wilson | |
| 5,454,827 A * | 10/1995 | Aust | A61B 1/0052 |
| | | | 606/174 |
| 5,462,527 A | 10/1995 | Stevens-Wright et al. | |
| 5,465,716 A * | 11/1995 | Avitall | A61M 25/0136 |
| | | | 606/41 |
| 5,480,382 A | 1/1996 | Hammerslag et al. | |
| 5,743,456 A * | 4/1998 | Jones | A61B 17/0684 |
| | | | 227/176.1 |
| 5,931,811 A | 8/1999 | Haissaguerre et al. | |
| 6,464,645 B1 * | 10/2002 | Park | A61B 8/12 |
| | | | 600/462 |
| 6,517,565 B1 * | 2/2003 | Whitman | A61B 17/1114 |
| | | | 600/146 |
| 6,666,854 B1 * | 12/2003 | Lange | A61B 17/2909 |
| | | | 606/1 |
| 6,945,956 B2 * | 9/2005 | Waldhauser | A61M 25/0012 |
| | | | 604/95.01 |
| 6,981,941 B2 * | 1/2006 | Whitman | A61B 34/71 |
| | | | 606/1 |
| 7,615,067 B2 * | 11/2009 | Lee | A61B 1/0057 |
| | | | 606/205 |
| 7,771,425 B2 * | 8/2010 | Dycus | A61B 18/1445 |
| | | | 606/49 |
| 7,842,028 B2 * | 11/2010 | Lee | A61B 17/3403 |
| | | | 606/1 |
| 7,862,554 B2 * | 1/2011 | Hegeman | A61B 1/0055 |
| | | | 606/1 |
| 8,465,442 B2 | 6/2013 | Freed | |
| 8,641,604 B2 * | 2/2014 | Golden | A61M 25/0147 |
| | | | 600/101 |
| 8,968,355 B2 * | 3/2015 | Malkowski | A61B 17/2909 |
| | | | 606/205 |
| 9,101,735 B2 * | 8/2015 | Rothe | A61M 25/0082 |
| 9,162,036 B2 * | 10/2015 | Caples | A61B 5/6857 |
| 9,498,112 B1 * | 11/2016 | Stewart | A61B 1/0676 |
| 9,657,817 B2 * | 5/2017 | Asselin | A61M 25/0136 |
| 9,968,343 B2 * | 5/2018 | Jeong | A61B 17/00234 |
| 10,016,187 B2 * | 7/2018 | Castro | A61B 17/29 |
| 10,448,964 B2 * | 10/2019 | Marczyk | A61B 17/2909 |
| 10,709,431 B2 * | 7/2020 | Parrott | A61B 17/29 |
| 10,799,675 B2 * | 10/2020 | Khuu | A61M 25/0147 |
| 10,799,676 B2 * | 10/2020 | Khuu | F16C 11/06 |
| 10,874,839 B2 * | 12/2020 | Matlock | A61B 17/24 |
| 2004/0127916 A1 * | 7/2004 | Bolduc | A61B 17/064 |
| | | | 606/151 |
| 2004/0181140 A1 | 9/2004 | Falwell et al. | |
| 2007/0010800 A1 * | 1/2007 | Weitzner | A61M 25/0147 |
| | | | 606/1 |
| 2007/0010801 A1 * | 1/2007 | Chen | A61M 25/0147 |
| | | | 606/1 |
| 2007/0135803 A1 * | 6/2007 | Belson | A61B 1/00154 |
| | | | 606/1 |
| 2007/0282371 A1 * | 12/2007 | Lee | A61B 17/29 |
| | | | 606/205 |
| 2008/0188890 A1 * | 8/2008 | Weitzner | A61B 1/018 |
| | | | 606/205 |
| 2008/0287862 A1 * | 11/2008 | Weitzner | A61B 34/71 |
| | | | 604/95.04 |
| 2009/0112230 A1 | 4/2009 | Jinno | |
| 2009/0171147 A1 * | 7/2009 | Lee | A61B 17/29 |
| | | | 600/137 |
| 2010/0004633 A1 * | 1/2010 | Rothe | A61B 1/0052 |
| | | | 604/528 |
| 2010/0004663 A1 | 1/2010 | Murphy et al. | |
| 2010/0011900 A1 | 1/2010 | Burbank | |
| 2011/0118710 A1 * | 5/2011 | Begemann | A61B 90/11 |
| | | | 606/1 |
| 2011/0230875 A1 | 9/2011 | Walberg et al. | |
| 2013/0012958 A1 * | 1/2013 | Marczyk | A61B 17/2909 |
| | | | 606/130 |
| 2013/0041314 A1 * | 2/2013 | Dillon | A61M 25/0147 |
| | | | 604/95.04 |
| 2014/0251042 A1 * | 9/2014 | Asselin | A61M 25/0136 |
| | | | 74/89 |
| 2015/0073434 A1 | 3/2015 | Simaan et al. | |
| 2015/0080792 A1 * | 3/2015 | Akutagawa | A61M 25/0136 |
| | | | 604/95.04 |
| 2015/0352728 A1 * | 12/2015 | Wang | A61B 1/0057 |
| | | | 74/490.04 |
| 2015/0366445 A1 * | 12/2015 | Rutgers | A61B 1/2676 |
| | | | 128/200.26 |
| 2016/0135914 A1 * | 5/2016 | Isoda | A61B 34/72 |
| | | | 606/130 |
| 2016/0309985 A1 * | 10/2016 | Akui | A61M 25/0138 |
| 2016/0367787 A1 | 12/2016 | Van Hoven et al. | |
| 2017/0065415 A1 * | 3/2017 | Rupp | A61F 2/2433 |
| 2017/0266413 A1 * | 9/2017 | Khuu | A61F 2/2427 |
| 2018/0071487 A1 * | 3/2018 | Khuu | A61M 25/0147 |
| 2018/0071488 A1 * | 3/2018 | Khuu | F16H 19/04 |
| 2018/0071489 A1 * | 3/2018 | Khuu | F16H 37/122 |
| 2018/0071490 A1 * | 3/2018 | Khuu | F16H 25/16 |
| 2018/0200416 A1 * | 7/2018 | Oza | A61B 1/2733 |
| 2019/0083748 A1 * | 3/2019 | Khuu | A61M 25/0136 |
| 2019/0192128 A1 * | 6/2019 | Xu | A61B 34/71 |
| 2020/0179114 A1 * | 6/2020 | Sheps | A61F 2/2427 |

FOREIGN PATENT DOCUMENTS

| | | | | |
|---|---|---|---|---|
| CN | 109009261 A | * | 12/2018 | ....... A61B 17/00234 |
| CN | 109009262 A | * | 12/2018 | ....... A61B 17/00234 |
| EP | 1 415 680 | | 5/2004 | |
| EP | 2452646 A1 | * | 5/2012 | ........ A61M 25/0136 |
| JP | H05-168716 A | | 7/1993 | |
| JP | 2015-205170 A | | 11/2015 | |
| KR | 20100100278 A | * | 9/2010 | ............ A61B 17/29 |
| WO | WO-2011108840 A2 | * | 9/2011 | ............ A61B 17/29 |
| WO | WO2017/043969 | | 3/2017 | |
| WO | WO-2017043969 A1 | * | 3/2017 | ............ A61B 17/29 |
| WO | WO-2017208400 A1 | * | 12/2017 | ............ A61B 17/29 |

* cited by examiner

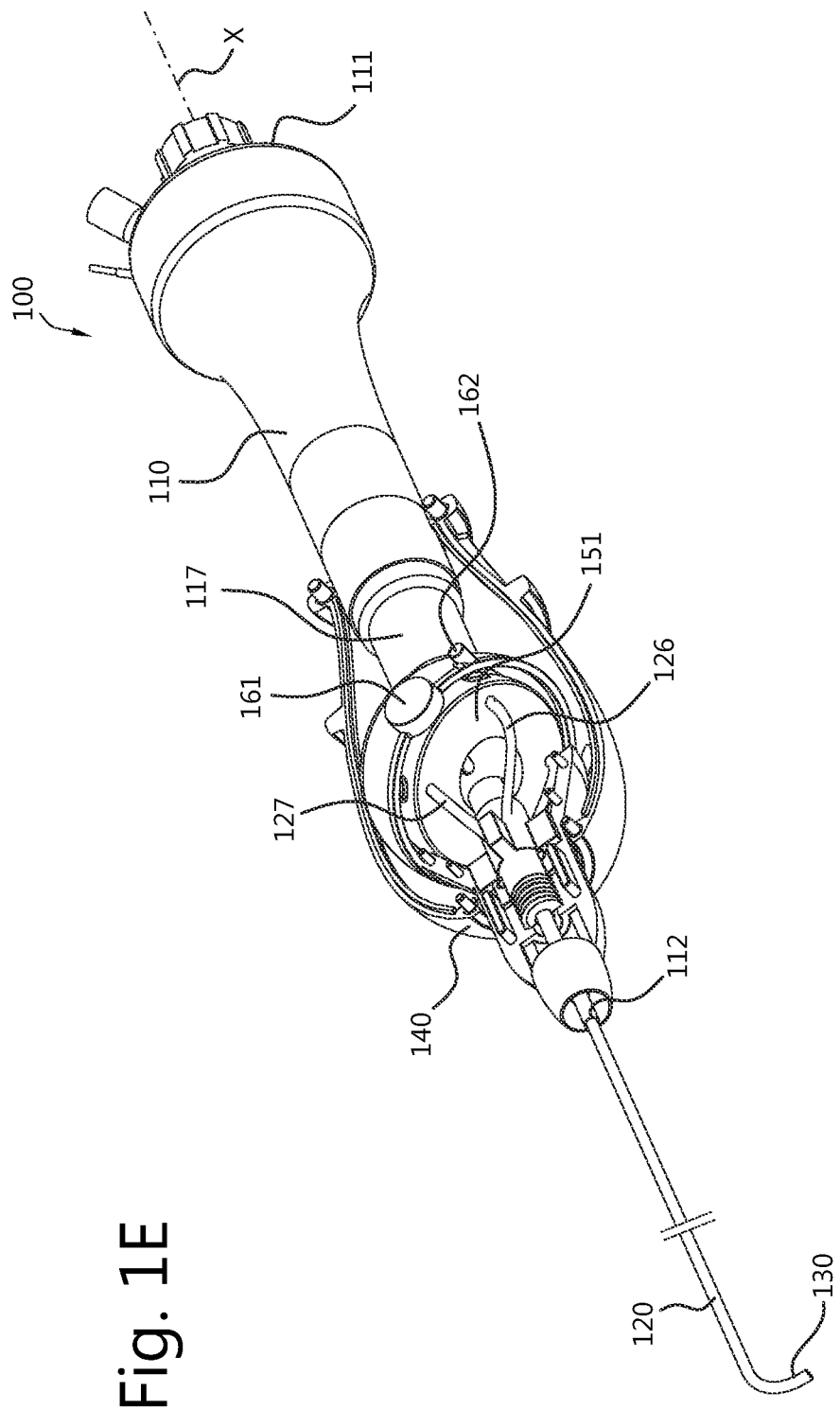

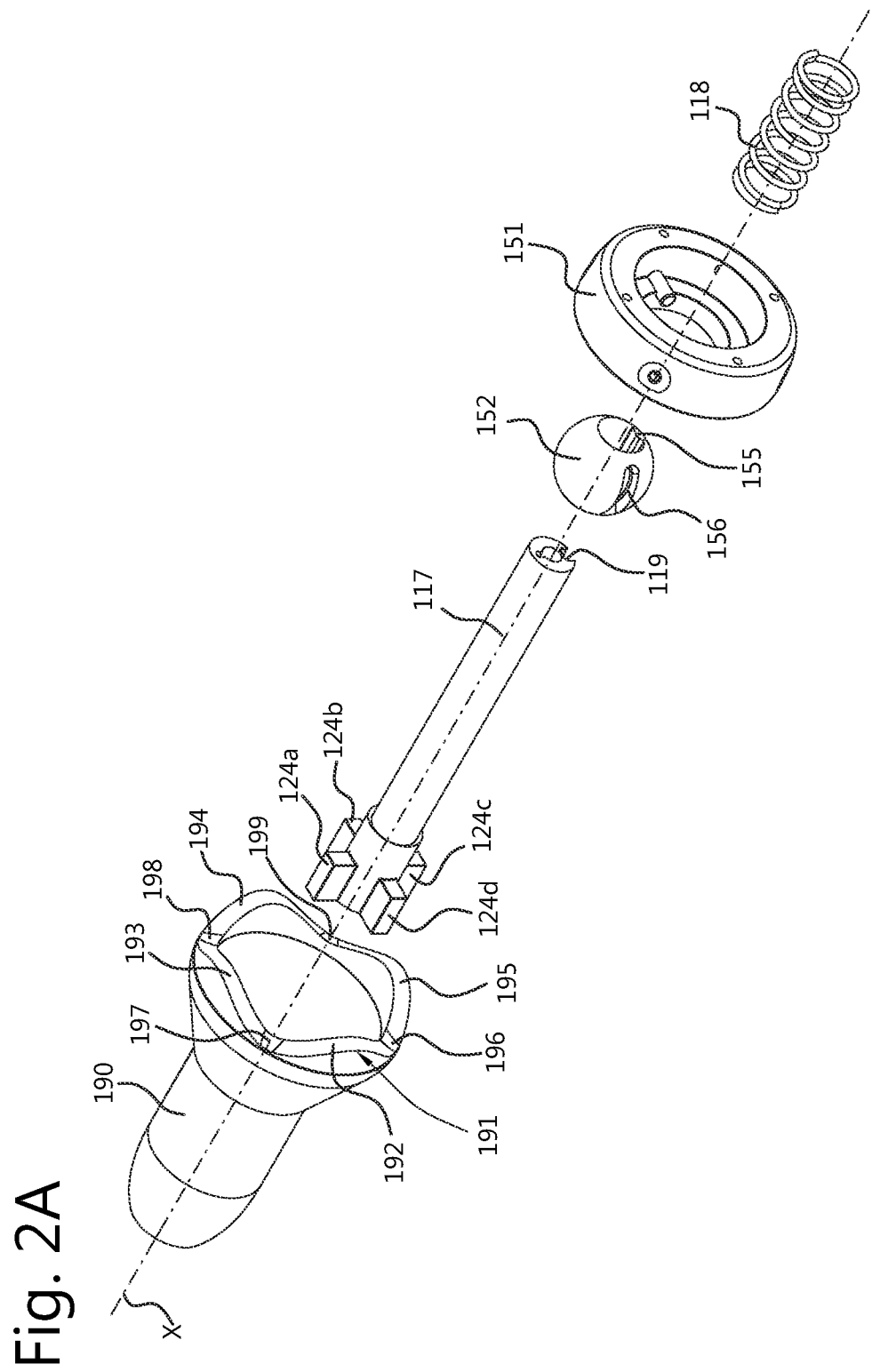

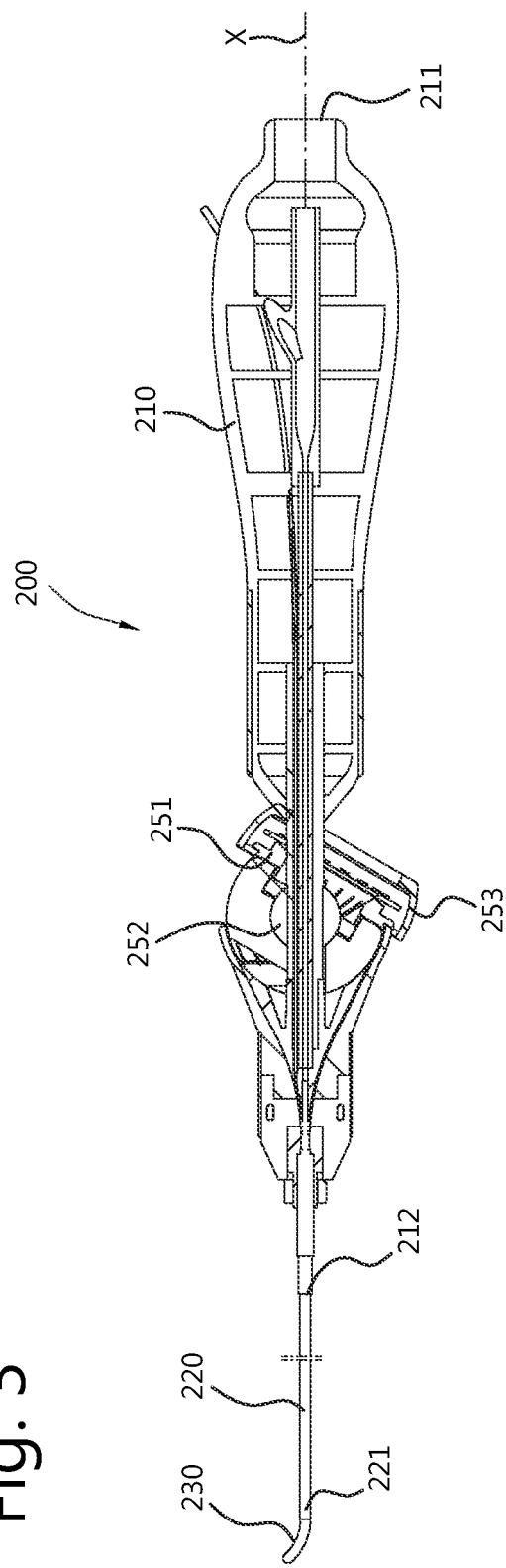

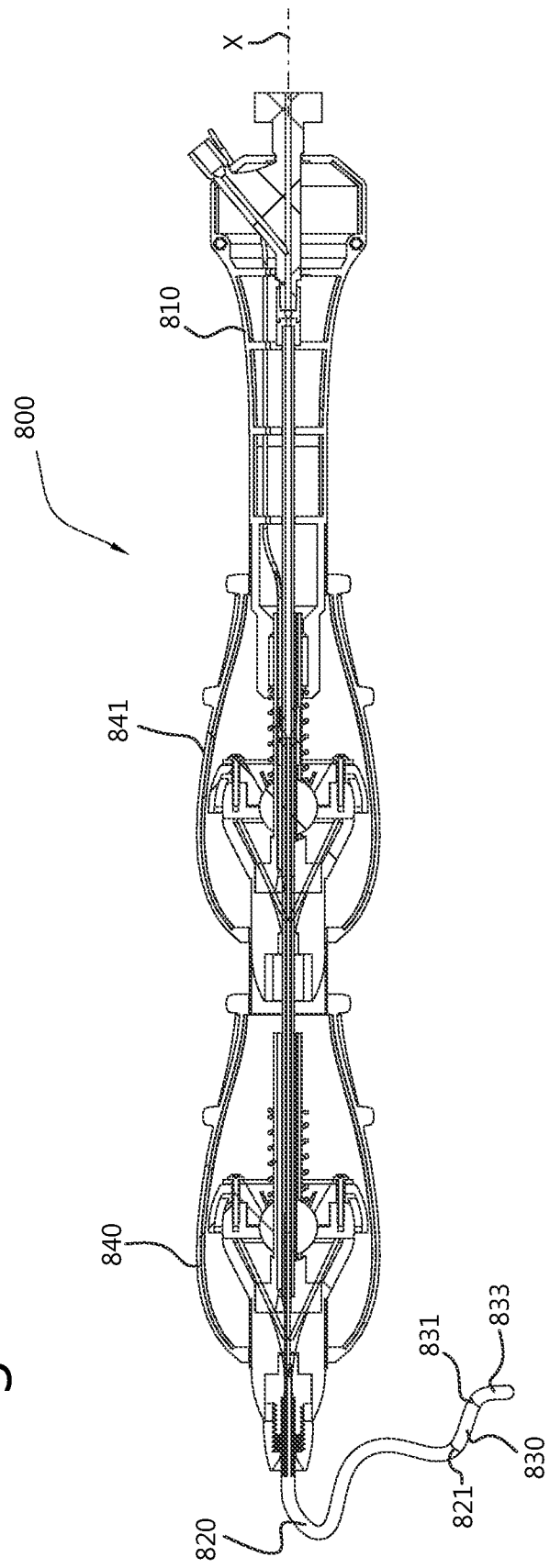

MEDICAL DEVICE WITH FLEXIBLE TIP

FIELD OF THE INVENTION

The present invention relates to a medical device comprising: a handle; a flexible tubing which extends from the handle and has a proximal end fixed to the handle; a flexible tip attached to the distal end of the flexible tubing and adapted for bending within multiple bending planes, wherein the handle is provided with one or more user operable controls for controlling an orientation of the flexible tip. The flexible tube and flexible tip preferably form part of a catheter for intravenous use.

BACKGROUND ART

From US 2007/0010801 a control for a medical device is known which includes an actuator that is moved by a physician to move a distal tip of the medical device in one or more of the up/down or left/right directions. The actuator can be moved forward or backward within a slot that extends longitudinally along the top of a cylindrical body of the control to move the distal tip of the medical device up or down. In addition, the actuator can be rotated in order to move the distal tip of the medical device in the left/right direction. By rotating the actuator the tip can be bent in left/right direction without affecting the orientation of the tip of the medical device the up/down direction, and vice versa.

Because sliding or rotational movement of the actuator only causes the tip to bend, the orientation of the exterior portion of the remaining part of the medical device through which the tip is connected to the control can remain substantially constant. In this manner, friction between a body to be treated/inspected and the exterior portion is substantially avoided. For instance, if the control is used to control the movement of the tip of a catheter within the veins of a patient, moving the tip will not cause substantial friction between the veins and the catheter other than at the tip.

The known control is particularly suited to be operated using one hand only, for either moving the tip in the left/right direction or in the up/down direction. The known control however does not allow very intuitive control of bending of the tip in other directions, as in general fine motor skills of a physician or assistant using the control are not predisposed to simultaneously working in two different planes, i.e. a plane in the up/down direction and a plane in the left/right direction.

It is an object of the present invention to provide a medical device with a flexible tip, having a more intuitive control for changing the orientation of the flexible tip.

It is a further object to provide such a device in which the orientation of the bending tip can be controlled without substantially changing the orientation of other exterior portions of the medical device which may come into contact with a patient's body.

SUMMARY OF THE INVENTION

To this end, according to a first aspect, the present invention provides a medical device comprising: a handle with a central axis; a flexible tubing which extends from the handle and has a proximal end fixed to the handle; a flexible tip attached to the distal end of the flexible tubing and adapted for bending within multiple bending planes; a tip actuator assembly for adjusting the bending plane of the tip relative to the distal end of the flexible tubing and for adjusting the degree of bending of said tip in the bending plane; a user operable control supported on the handle and moveable in a first, rotational direction relative to the handle and to the tip actuator assembly around an axis of rotation for causing the tip actuator assembly to adjust the bending plane of the tip, wherein the user operable control further is moveable relative to the handle and to the tip actuator assembly along a second, substantially linear direction towards and away from the proximal end of the flexible tubing, for causing the tip actuator assembly to adjust the degree of bending of the tip in the bending plane without adjusting the bending plane and substantially without rotating the flexible tubing.

The medical device provides a user operable control which can be operated single-handedly and allows intuitive rotation of the bending plane of the tip simply by rotating the user operable control. The degree of bending of the tip in its bending plane can easily be adjusted by moving the user operable control along the second direction which is different from the first direction. The user operable control preferably is moveable along the second direction between a first position which corresponds to a maximum bending of the tip towards one side of the bending plane, and a second position which corresponds to a maximum bending of the tip towards another side of the bending plane, wherein an intermediate position for the control exist in which the tip is coaxial with the distal end of the flexible tubing to which it is attached. Alternatively, the user operable control may be movable along the second direction between a first position which corresponds to a maximum bending of the tip towards one side of the bending plane, and a second position which corresponds to no bending of the tip, such that the tip is substantially coaxial with the distal end of the flexible tubing to which it is attached. Especially in the latter case, the first and second positions preferably correspond respectively to a maximum position in which the user operable control can physically be moved along the second direction towards and away from the proximal end of the flexible tubing. In this manner, the tip can be oriented in a position in which it is substantially coaxial with the distal end of the flexible tubing, by moving the user operable control along the second direction until it has reach the second position and can be moved not further in the same direction.

As movement of the user operable control relative to the handle affects the orientation of the tip without substantially affecting the orientation of the tubing, friction between the tubing and a patient's body during adjustment of the orientation of the tip relative to the end of the tubing to which it is attached is substantially avoided. Though the tubing according to the invention is flexible, allowing it to be inserted into a patient's body, e.g. intravenously, through the lungs or through the oesophagus, and follow passages defined by the body, it is conceivable to instead use a substantially rigid tubing, e.g. when the medical device is to be used on a part of a patient's body that is readily accessible from outside of the body.

The user operable control is preferably shaped as a single user operable control unit, which is rotatable as a unit in the first, rotational direction without being moved along the second direction, and which is moveable as a unit along the second direction without rotating along the first direction. Such a unit can be particularly easily manipulated when formed as a circumferential hollow unit through which the central axis extends, the unit preferably having an outer diameter or outer diameters in the range of 2,5 cm to 6 cm along planes normal to the central axis. During use, a user, such as a physician, will generally hold the handle substantially still using one hand, while controlling the bending plane and degree of bending of the tip using fingers of the one hand or using the other hand, and while keeping an eye on a display which shows the tip relative to a patient's body. It is therefore desirable that the user can determine a rotational position of the user control relative to the handle without looking at either. To this end, in an embodiment, the user operable control is provided with tactile markings, such as protrusions and/or depressions, on its exterior. Such markings allow the user to quickly determine a rotation of the user operable control relative to the handle without looking, even after having temporarily having lost contact with the user operable control. The handle may be provided with tactile markings for this purpose as well.

In an embodiment the second direction is a linear direction parallel to the central axis. This allows the user operable control to be moved linearly along the central axis for adjusting the tip's degree of bending.

In an embodiment the user operable control is provided with a locking mechanism for locking movement in its rotational direction of movement, and/or for locking movement along its second direction of movement. This facilitates temporarily keeping the bending plane and/or the degree of bending constant. The locking mechanism preferably comprises a clamp adapted for releasably clamping a portion of the handle to block rotation and/or translation of the user operable control relative to the handle. It will be clear that when the locking means do not clamp the handle, it does not block movement of the user operable control relative to the handle.

In an embodiment the tip actuator assembly comprises: a tilting plate which is tiltable relative to the central axis for adjusting the bending plane of the tip relative to the distal end of the flexible tubing and the degree of bending in said bending plane; and multiple steering cables which are partially arranged within the flexible tubing and are connected at one end to the flexible tip and connected at another end to the tilting plate. By operating the user operable controls the tilting plate can be moved for adjusting the bending plane and the degree of bending of the tip. The medical device is preferably provided with a blocking element, e.g. a groove or splice, which cooperates with a complementary splice of groove in the tilting plate for preventing rotation of the tilting plate around the central axis.

In an embodiment the user operable control is mechanically connected to the tilting plate via a mechanical link mechanism which is adapted for converting movement of the user operable control in the first rotational direction to a tilt of the tilting plate for adjusting the bending plane of the tip, and for converting movement of the operable control along the second direction to a movement of the tilting plate for adjusting the degree of bending of the tip in the bending plane. Thus, a rotational movement of the user operable control around the axis of rotation is converted to a different movement of the tilting plate, such as tilt of the plate around an axis different from the axis of rotation and/or translation of the tilting plate along the central axis. Likewise, a movement of the user operable control along its associated second direction of movement results in a movement of the tilting plate in a different direction than the second direction, such as tilt of the plate relative to the central axis and/or translation of the tilting plate along the central axis.

In an embodiment the tilting plate is axially moveable along the central axis, the medical device further comprising a blocking element that is fixed with respect to the central axis and adapted for preventing rotation of the tilting plate around the central axis. As the tilting plate can thus move along the central axis of the handle, buckling of any steering cable connected to the titling plate at a fixed point is substantially reduced when the tilting plate is tilted such that the fixed point is moved closer to the proximal end.

In an embodiment the titling plate has an annular outer edge, the linking mechanism comprising a ring in which the outer annular edge is accommodated such that the ring and tilting plate are rotatable relative to each other around a central axis of the ring while translation between the ring and titling plate along said central axis of the ring is substantially blocked. The ring, which in turn is connected to the user operable control, can thus be rotated around the central axis for one or more revolutions, without causing rotation of the tiling plate around the central axis.

In an embodiment an outer surface of the ring comprises a first projection extending in a first plane parallel to and intersecting the central axis of the handle, and adapted for sliding and rotating in a corresponding slot of the user operable control, or vice versa, so that rotational movement of the user operable control causes tilting of the tilting plate for adjusting the bending plane of the tip. The slot preferably has a longitudinal axis parallel to the central axis of the handle.

In an embodiment the outer surface of the ring comprises a second projection extending substantially parallel to the first projection and spaced apart from said first plane, and adapted or sliding and rotating in a corresponding slot of the user operable control, or vice versa, so that movement of the user operable control along the second direction causes tilting of the tilting plate for adjusting degree of bending of the tip in the bending plane.

In an embodiment the user operable control is moveable in the first, rotational direction relative to the handle and to the tip actuator assembly around an axis of rotation for causing the tip actuator assembly to adjust the bending plane of the tip without adjusting the degree of bending of the tip in said plane. The bending plane of the tip and its degree of bending can thus intuitively be controlled independent from each other.

In an embodiment the handle comprises an abutment section with a circumferential edge arranged for abutment with at least a portion of a facing edge of the tilting plate, wherein the circumferential edge comprises a number of crests facing the tilting plate and a corresponding number of valleys between two neighbouring crests, wherein the number of valleys equals the number of steering cables, and wherein the valleys are arranged in line with the points of attachment of the steering cables to the tilting plate. The crests and valleys are adapted for compensating a change in distance between the points of attachment of the steering cables to the steering plate and the proximal end, during rotation of the user operable control. In particular, the crests and valleys thus ensure that the bending plane of the tip can be adjusted by rotation of the user operable control, substantially without adjusting the degree of bending of the tip.

In an embodiment the tip actuator assembly comprises electromechanical actuators arranged for setting the bending plane of the flexible tip and a degree of bending of the flexible tip within said plane in proportion to an electrical control signal provided to the electromechanical actuators by the first and second user operable controls. Thus electromechanical actuators are used, e.g. rather than a tilting plate, for adjusting the bending plane of the tip and the degree of bending of the tip in its bending plane.

In an embodiment the first, rotational, direction is a direction of rotation around an axis substantially perpendicular to the central axis. Thus, the user operable control can be rotated around an axis perpendicular to the central axis for adjusting the tip's bending plane.

According to a second aspect, the present invention provides a medical device comprising: a handle with a central axis; a flexible tubing which extends from the handle and has a proximal end fixed to the handle; a flexible tip attached to the distal end of the flexible tubing and adapted for bending within multiple bending planes; a tip actuator assembly for adjusting the bending plane of the tip relative to the distal end of the flexible tubing and for adjusting the degree of bending of said tip in the bending plane; a first user operable control supported on the handle and moveable in a first, rotational direction relative to the handle and to the tip actuator assembly around an axis of rotation for causing the tip actuator assembly to adjust the bending plane of the tip without adjusting the degree of bending of the tip in said plane and substantially without rotating the flexible tubing; and a second user operable control supported on the handle and moveable relative to the handle and to the tip actuator assembly along a second direction towards and away from the proximal end of the flexible tubing, for causing the tip actuator assembly to adjust the degree of bending of the tip in the bending plane without adjusting the bending plane. The medical device provides two separate user operable controls which allow intuitive rotation of the bending plane of the tip simply by rotating the user first operable control, while the degree of bending of the tip in its bending plane can easily be adjusted by moving the user second operable control along the second direction which is different from the first direction.

In an embodiment the first and second user operable controls are spaced apart from each other on the handle and are adapted to be operated by a user independent from each other.

In an embodiment the second user operable control is mechanically connected to the first user operable control such that the second direction depends on a rotational orientation of the first user operable control relative to the handle. For instance, the second user operable control may be supported or attached to the first user operable control in such a manner that rotation of the first user operable control around its axis of rotation also results in rotation of the second user operable control around the axis of rotation, wherein the second user operable control is moveable in the second direction without changing the position of the first user operable control.

In an embodiment the tip actuator assembly comprises electromechanical actuators arranged for setting the bending plane of the flexible tip and a degree of bending of the flexible tip within said plane in proportion to an electrical control signal provided to the electromechanical actuators by the first and second user operable controls.

According to a third aspect, the present invention provides a medical device comprising: a handle with a central axis; a flexible tubing which extends from the handle and has a proximal end fixed to the handle; a flexible tip attached to the distal end of the flexible tubing and adapted for bending within multiple bending planes; a tip actuator assembly for adjusting the bending plane of the tip relative to the distal end of the flexible tubing and for adjusting the degree of bending of said tip in the bending plane; a first user operable control supported on the handle and moveable in a first, rotational direction relative to the handle and to the tip actuator assembly around an axis of rotation for causing the tip actuator assembly to adjust the bending plane of the tip without adjusting the degree of bending of the tip in said plane and substantially without rotating the flexible tubing; and a second user operable control supported on the handle and moveable relative to the handle and to the tip actuator assembly along a second, substantially linear, for causing the tip actuator assembly to adjust the degree of bending of the tip in the bending plane without adjusting the bending plane.

Below, a number of embodiments are described which the skilled person will understand may be embodiments of the invention according to the first, second and/or third aspect.

In an embodiment in which the medical device is provided with electromechanical actuators for adjusting the bending plane and degree of bending of the tip, preferably the user operable control or controls are adapted for providing electrical signals to the controller indicative of a position and/or orientation of the user operable control or controls, the medical device further comprising a controller adapted for controlling the actuators for setting the bending plane of the flexible tip and a degree of bending of the flexible tip within said plane based on said signals.

In an embodiment, the medical device is a portable medical device, wherein the handle is adapted to be hand held. In case the medical device comprises a single user operable control for controlling both the bending plane and degree of bending of the tip, the handle of the medical device is adapted to be held in one hand while the user operable control controlled by the fingers of the same hand, or by the other hand. In case the medical device comprises two separate user operable controls, both the first and second user operable control are preferably arranged on the handle in such a manner that that can be simultaneously controlled single-handedly, e.g. within 8 cm from each independent of the positions and orientations of the first and second user operable controls.

In an embodiment the second direction is a linear direction relative to the handle and to the tip actuator assembly. This allows a user to intuitively adjust the degree of bending of the tip by moving the second user operable control in the linear direction.

In an embodiment, the electromechanical actuators are arranged within or at the flexible tip, wherein the flexible tubing is preferable provided with conductors electrically connecting the controller to the actuators.

In an embodiment the electromechanical actuators comprise shape memory wire actuators arranged in or at the flexible tip. An example of such a shape memory wire actuator is a nitinol wire adapted for changing its shape depending on a voltage difference that is applied thereto.

In an embodiment the medical device further comprises multiple steering cables which are partially arranged within the flexible tubing and are connected at one end to the flexible tip and at another end to one or more of the electromechanical actuators.

In an embodiment the multiple steering cables each comprise a section which is surrounded by a flexible encapsulation that extends from the proximal end of the tubing to the point of attachment of said steering cable within the handle, wherein the flexible encapsulation is adapted for allowing sliding movement of the section along the encapsulation while the encapsulation expands or contracts along the direction of sliding movement. The encapsulation prevents the steering wires from buckling and/or catching within the handle, and protect the steering cables from particles which may cause friction. The extent to which the encapsulation expands or contracts preferably is smaller than the change in distance between the first and second end of the steering wires section. The point of attachment of a steering cable may be its point of attachment to the tilting plate if a tilting plate is used, or its point of attachment to an electromechanical actuator arranged within the handle, if electromechanical actuators are used for adjusting the bending and degree of bending of the tip.

In an embodiment the encapsulation comprises one or more of: a coil spring, an elastic sheathing, a bellows, a braided tube.

In an embodiment two or more of the steering cable sections are arranged within a single flexible encapsulation.

In an embodiment the flexible encapsulation extends within substantially the entire length of the tubing section to the flexible tip.

In an embodiment the flexible tip comprises a first flexible tip portion attached to the distal end of the flexible tubing and a second flexible tip portion attached to a distal end of the first flexible tip portion, wherein the tip actuator assembly is adapted for adjusting the bending plane and degree of bending of the first flexible tip portion, the medical device comprising a second tip actuator assembly for adjusting a bending plane of the second tip portion relative to the distal end of the first flexible tip portion and for adjusting the degree of bending of said second tip portion in the bending plane of the second tip portion. The second tip actuator assembly is preferably controlled using a further user operable control or a further first and a further second user operable control as described herein.

In a further embodiment thereof, the medical device comprises a further user operable control or further user operable controls supported on the handle axially rearward of the user operable control with respect to the proximal end, and moveable relative to the handle and to the second tip actuator assembly for causing the second tip actuator assembly to adjust the bending plane of the second tip portion without adjusting the degree of bending of the second tip portion in its corresponding bending plane and for causing the second tip actuator assembly to adjust the degree of bending of the second tip portion in its corresponding bending plane without adjusting the bending plane and substantially without rotating the flexible tubing, and wherein the user operable control and the further user operable control or controls are movable independent from each other relative to the handle. The second tip portion can thus be moved without moving the first tip portion by means of the further user operable control relative to the handle. Movement of the user operable control which controls the first tip portion, will however cause the second tip portion to move in conjunction with the first tip portion.

SHORT DESCRIPTION OF DRAWINGS

The present invention will be discussed in more detail below, with reference to the attached drawings, in which:

FIGS. 1A-1G show a medical device according to a first embodiment of the invention;

FIGS. 2A-2C show a detail an abutment section for abutment with a tilting plate, as may be used in a medical device according to the invention;

FIG. 3 shows a medical device according to a second embodiment of the invention;

FIG. 5 shows a medical device according to the invention comprising a tip with two flexible tip portions which are controllable using corresponding user operable controls;

DESCRIPTION OF EMBODIMENTS

Figure 1A:
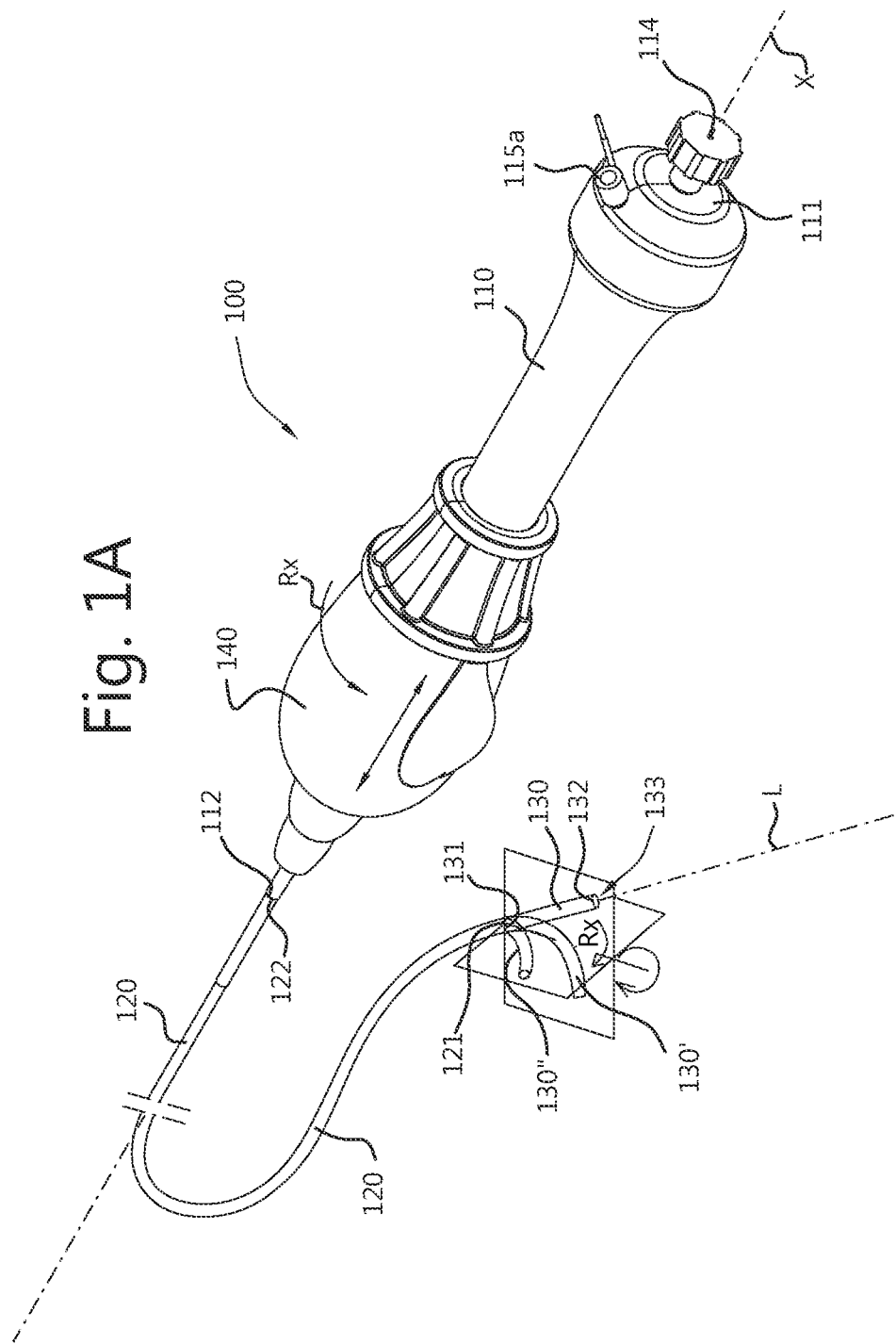

FIG. 1A shows an isometric view of a medical device 100 according to a first embodiment of the present invention. The device comprises a handle 110 with a central axis X which extends between a first end 111 and an opposite second end 112 of the handle. From the second end 112 of the handle a flexible tubing 120 extends, the flexible tubing being attached at its proximal end 122 to the handle in such a manner that the proximal end is fixed and stationary with respect to the second end 112 of the handle. At the opposite, distal end 121 of the flexible tubing, a flexible tip 130 is attached which can be bend relative to the distal end 121 by moving user operable control 140 relative to the central axis X of the handle 110. A first end 131 of the tip is attached to the distal end 121 of the tubing. Though in the embodiment shown, at its other end 132 the tip comprises a through opening 133 for allowing a substance or element to project therefrom or exit there through, it will be appreciated that in another embodiment the tip may be an ablation tip, which may be closed at its other end. For example, a substance such as a contrast liquid may be injected into inlet ports 114 or 115a, to pass through the medical device and flexible tubing 120 to exit the tip at opening 133. Examples of elements which may project from the through opening 133 is a guide wire and/or an optical fibre, which may be inserted into the flexible tubing through inlet port 114 or 115a, of the handle.

The degree of bending of the tip 130 within its bending plane is adjusted when the user translates the control 140 along a first direction, i.e. the direction in which the central axis X extends, relative to the handle 110. When the user operable control 140 is in a position along the central axis X closest to the proximal end 112 of the handle, there is no bending of the tip in its bending plane, i.e. the tip extends along a substantially straight line L from its first end 131 to its second end 132, as is the case for tip 130 of FIG. 1A. When the user operable control is in a position along the central axis X furthest away from the proximal end 122 of the tubing, the bending of the tip 130 in its bending plane is maximized. In the present example when the bending of the tip in its bending plane is maximized the longitudinal lines through first end 131 of the tip and the second end 132 of the tip are at an angle of about 90° to each other. In FIG. 1A, the tips 130' and 130" shown in dotted lines respectively are at angles of 45 and 90 within their corresponding bending planes.

When a user rotates the user operable control 140 relative to the handle 110 around its central axis X along a second, rotational direction Rx, the second end 131 of the tip is moved correspondingly such that bending plane of the flexible tip relative to the distal end 121 of the flexible tubing is adjusted with respect to the distal end 121. The orientation of the bending plane of the tip relative to the distal end 121 of the tubing corresponds to the rotation of the user operable control 140 around the handle 110. Thus, rotation of the user operable control 140 along the direction of rotation Rx relative to the handle by a number of degrees will cause the bending plane of the flexible tip 130 to be adjusted relative to the distal end 121 of the tubing by the same number of degrees. When, starting from an orientation in which the tip 130 is in an initial bending plane, the user operable control 140 is made to make one or more complete revolutions around the handle, the tip will be back in its initial bending plane.

The user operable control 140 can be rotated in the first, rotational direction Rx without being moved along the central axis X, and is moveable along the central axis X without rotating along direction Rx about the central axis X. Though the bending plane of the tip 130 relative to the distal end 121 can be adjusted, it will be clear that the first end 131 of the tip remains attached to the distal end 121 of the tubing and does not rotate relative thereto.

Figure 1B:
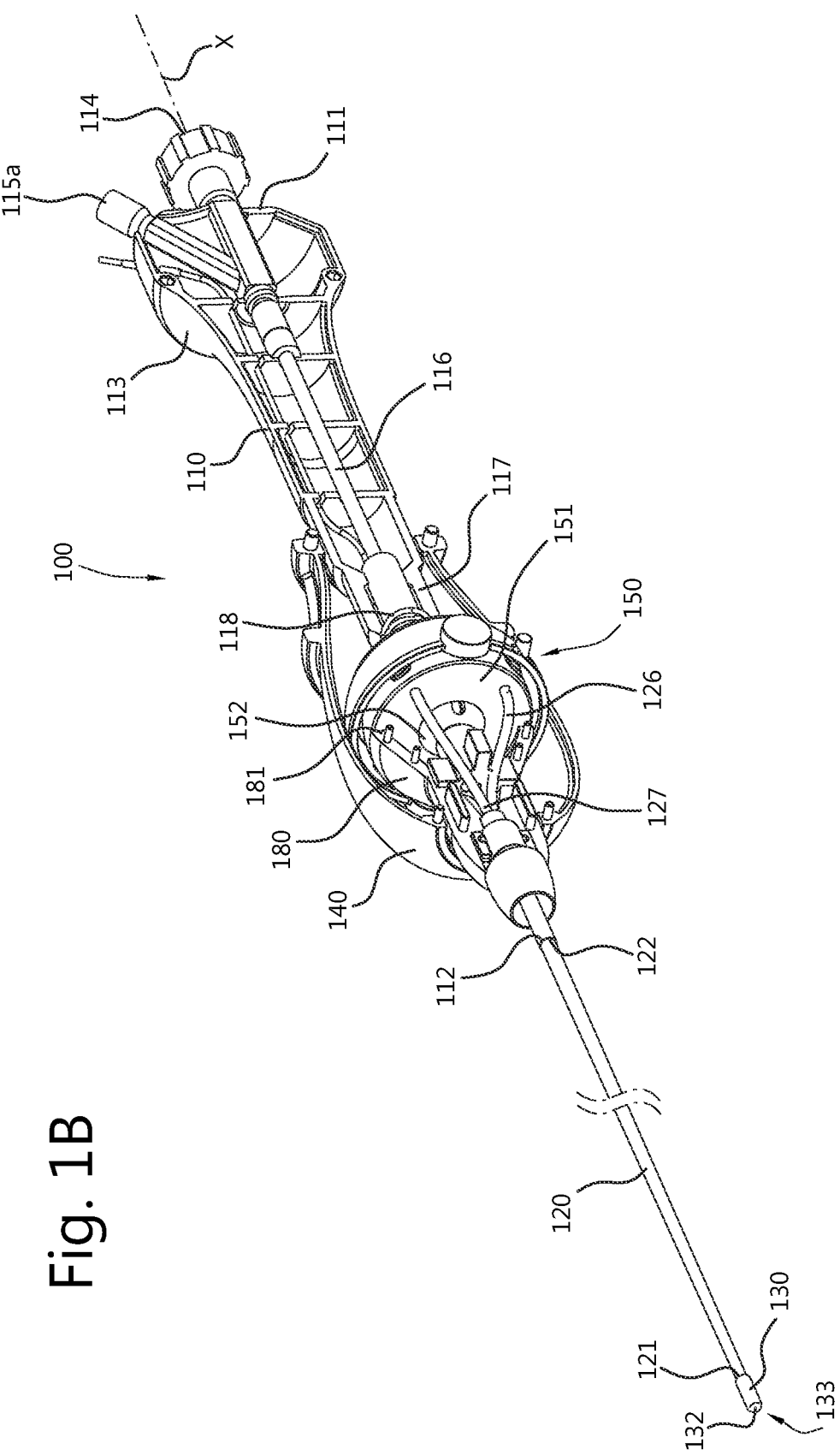

FIG. 1B shows an isometric view of the medical device 100, in which the handle 110 and the user operable control 140 are shown partially cut-away to provide a view on the interior of the device. The user operable control can be translated as a single unit along the X-axis of the handle, which X-axis also forms the axis of rotation when the user operable control 140 is rotated in direction of rotation Rx. The handle 110 extends from its first end 111 to its opposite second end 112 and through the user operable control 140. The handle has an outer portion 113 for being held by a user, a support portion 117 which lies partially within the user operable control 140 and supports the second end 112 of the handle, and a guide tube 116 which is connected to inlet ports 114, and 115a and extends through the support portion 117 to the second end 112 of the handle. Wires, such as guidewires and/or optical fibres, can be inserted through the ports 114, 115a, to pass through the guide tube 116 and flexible tubing 120 up to and/or through the opening 133 at the second end 132 of the flexible tip. Alternatively, liquid such as contrast liquid can be injected through the ports, to be delivered through the opening 133 at end 132 of the tip.

Within the user operable control 140 a tip actuator assembly 150 is provided which is mechanically connected to the user operable control 140 and is moveable relative thereto and relative to the handle 110. The assembly comprises a tilting plate 151 which is tiltably supported on the handle with respect to the central axis X by a spherical joint 152. The spherical joint 152 in turn is slidably attached to the support portion 117 and supported thereby. When the spherical joint is slid along the support portion 117, steering cables 126, 127 that are connected to the tilting plate can be tensioned or relaxed without changing the tilt of the tilting plate. The joint 152 is blocked from rotating relative to the support portion 117 around the central axis X, e.g. by means of a splice and corresponding groove in the spherical joint and the support portion 117. The handle 110 further comprises an abutment section 180 with a circumferential edge 181, against which edge the tilting plate 151 may abut. A spring 118, which at one end is blocked from moving by the support section 117 and another end lying against the spherical joint 152, biases the spherical joint towards the abutment section 180, so that the tilting plate is in circumferential abutment with the circumferential edge 181.

Figure 1C:
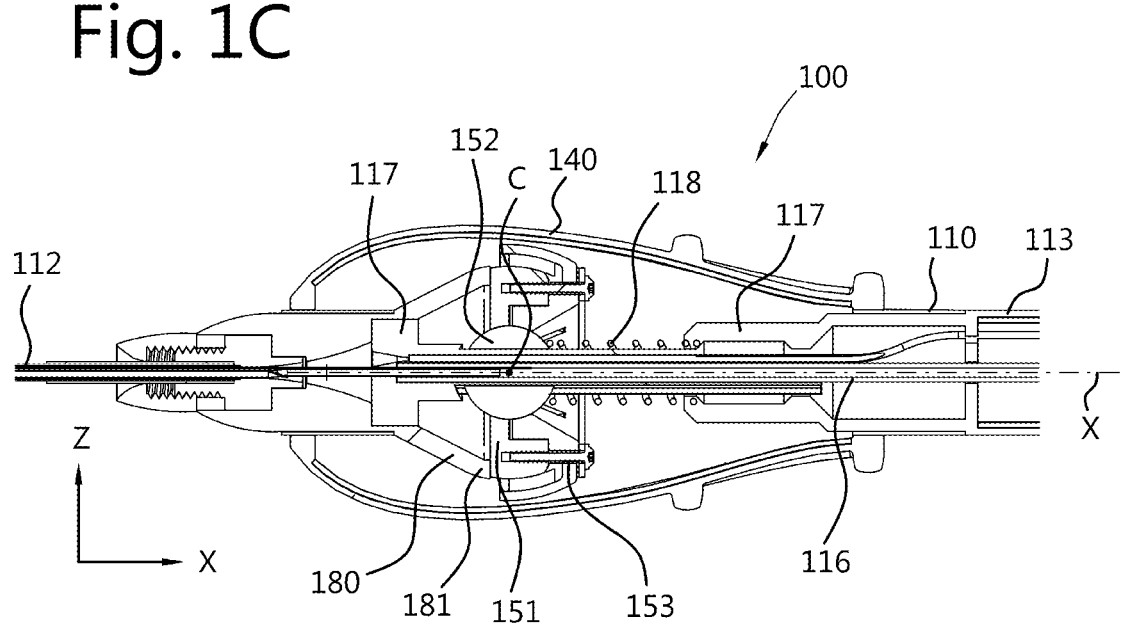
Figure 1D:
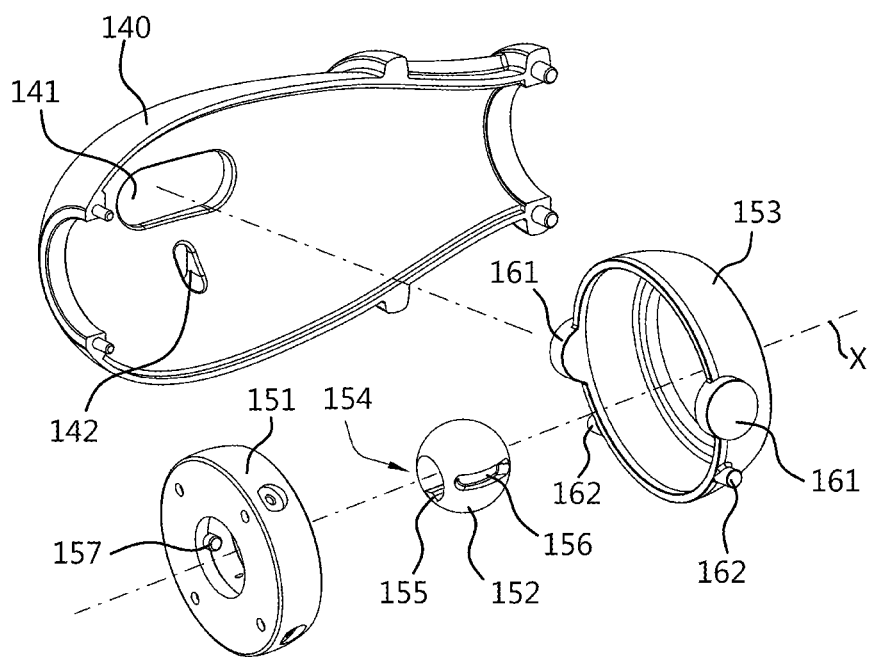

FIG. 1C schematically shows a cross-sectional side view of a portion of the medical device 100 of FIG. 1B in which the tip actuator assembly comprising the tilting plate 151 that is tiltably supported on the spherical joint 152 is shown in greater detail, in which the steering cables that are connected to the tilting plate however have not been shown for reasons of clarity. In both FIGS. 1B and 1C, the user operable control 140 is in a position and orientation with respect to the central axis X such that the tilting plate 151 is oriented substantially normal to the central axis X, and the flexible tip 130 extends in a substantially straight line between its first end 131 and its second end 132. However, when the tilting plate is tilted around an axis through centre point C of spherical joint 152 perpendicular to the central axis X, only a portion of the circumferential edge 181 will be in contact with the tilting plate. Referring to FIG. 1D, it can be seen that the tip actuator assembly 150 further comprises a linking mechanism with a ring 153 within which an annular edge of the tilting plate 151 is accommodated. The ring 153 is slidably rotatable relative to the tilting plate 151 around a central axis of the tilting plate, which central axis in the orientation of the tilting plate shown in FIG. 10 coincides with the central axis X. The outer edge of the tilting plate 151 is accommodated in the ring 153 in such a manner that tilt of the ring results in a corresponding tilt of the tilting plate 151 and that rotation of the ring 153 around the central axis X results in a change in orientation of the tilting plate without a corresponding rotation of the tilting plate around the central axis X.

FIG. 1D shows a partially cut-away view of the user operable control 140, and an exploded view of the tilting plate 151, the spherical joint 152 and the ring 153. The spherical joint 152 has a through opening 154 with a splice 155 for cooperation with a ridge along support portion 117, to allow the joint to slide along the support portion 117 without rotating relative to the central axis X. On its exterior the spherical joint 152 comprises slots 156 for cooperation with pins 157 in the tilting plate, for allowing the tilting plate 151 to tilt while blocking rotation of the titling plate around the central axis X. The tilting plate can thus tilt with respect to the support 117 while being rotationally fixed with respect to the support portion 117 around the direction of rotation Rx.

On its interior surface the user operable control 140 comprises two first elongated slots 141, only one of which is shown, which extend in a plane through the central axis X and are adapted for slidably and rotationally accommodating therein first pins 161 of the ring 153. The user operable control further comprises on its interior surface two second elongated slots 142, only one of which is shown, which extend in the direction of the circumference of the user operable control and are adapted for slidably and rotationally accommodating therein second pins 162 of the ring 153. The first pins 161 and corresponding first slots 141 thus extend parallel to the central axis X and in a plane through said central axis. The second pins 162 are spaced apart from said plane but extend parallel to the first pins 161. When the user operable control is rotated around the central axis, the first pins 161 which are accommodated in first slots 141 will cause the ring to rotate along with the user operable control in the circumferential direction to change the bending plane of the tip. When the user operable control is linearly moved along the central axis, the second pins 162 will engage the second slots 142 and cause the tilting plate to tilt around the first pins 161, resulting in a corresponding difference in degree of bending of the tip in its bending plane.

FIG. 1E shows an isometric view of the medical device of FIG. 1A, with the user operable control 140 shown partially cut-away. With respect to FIG. 1A the user operable control has been rotated about 45° around the central axis X, and translated towards the first end 111 of the handle, resulting respectively in a corresponding 45° change in bending plane of the tip 130 and in a tilt of the tilting plate 151 around pins 161.

Figure 1F:
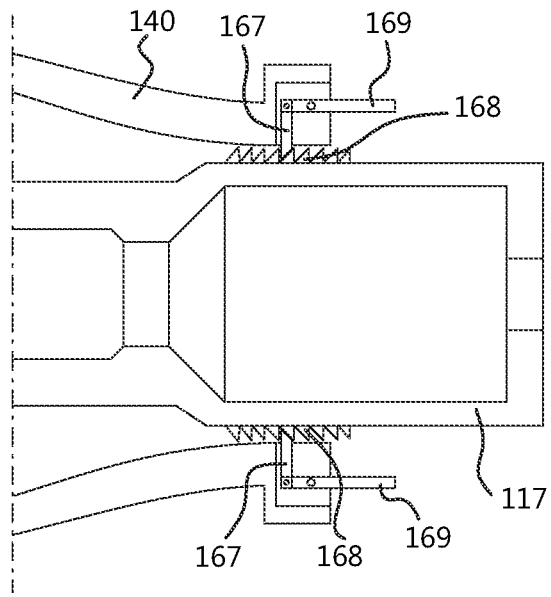
Figure 1G:
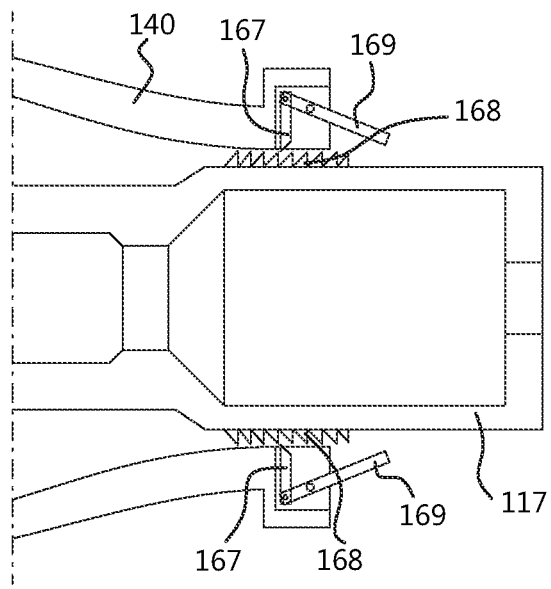

FIGS. 1F and 1G respectively shows a locking mechanism as may be used in a medical device 100 of FIG. 1A. The locking mechanism is adapted 167, 168 for blocking rotational as well as translational movement of the user operable control 140 with respect to the handle. FIG. 1F shows the mechanism 167, 168 in a locked state in which elements 167 of the user operable control 140 engage elements 168 on the support section 117 of the handle. Elements 167 are hingedly connected to levers 169 which are part of the user operable control 140 and by means of which the elements 167 can be moved relative to elements 168 between an engaging position and a disengaged position. When the levers are in a locking position, as shown in FIG. 1F, elements 167 engage with elements 168 and rotational as well as translation movement of the user operable control 140 relative to the handle 110 is locked. FIG. 1G shows the lever in a released position, in which the elements 167, 168 are disengaged such that both rotational and translational movement of the user operable control is possible. When the lever 169 is in an intermediate position between the engaged and released position, rotation of the user operable control is possible while translation of the user operable control relative to the handle is blocked. Though not shown, it will be appreciated that a locking mechanism while allows translation while blocking rotation of the user operable control relative to the handle is conceivable as well.

Figure 2B:
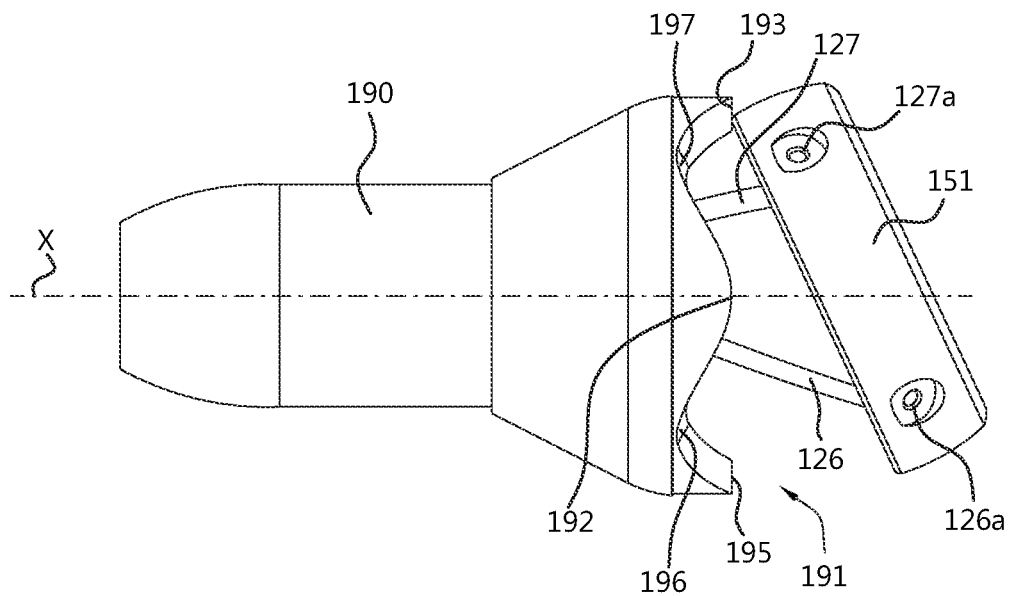
Figure 2C:
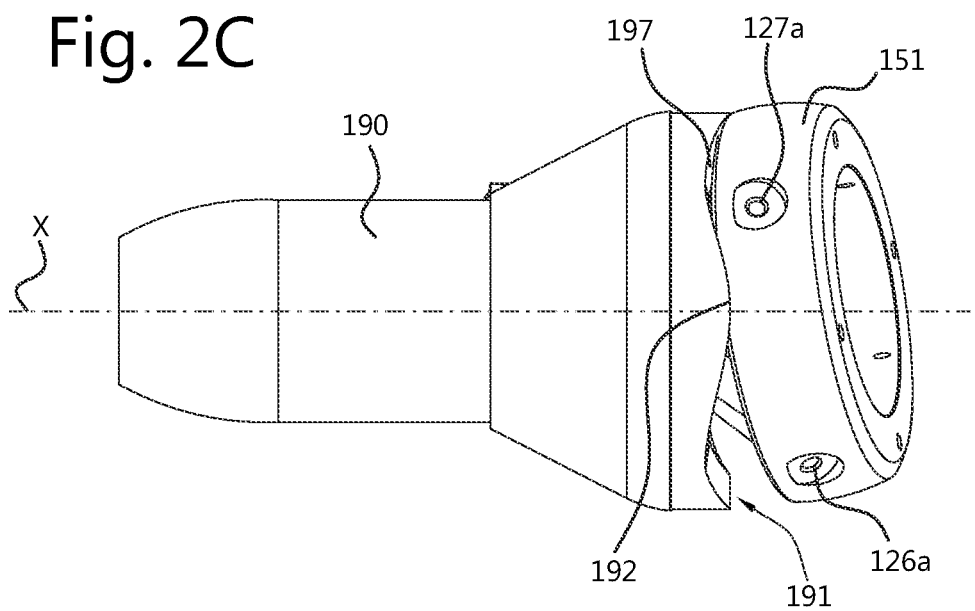

FIG. 2A-2C show an alternative abutment section 190 which preferably takes the place of abutment section 180 of FIGS. 1A-1D. The exploded view of FIG. 2A further shows part of support section 117, the tilting plate 151, the spherical joint 152, and the spring 118. The abutment section 190 comprises a wave shaped circumferential edge 191 for abutting a facing surface of the tilting plate 151. In the embodiments of FIGS. 1A-1D and FIGS. 2A-2C, the tilting plate 151 is provided with four steering cables which are spaced equidistantly at 90 degree intervals along the circumference of the tilting plate, two of which cables 126, 127 are shown in FIG. 2B respectively attached to the tilting plate 151 at positions 126a and 127a. When titling plate is at a tilt, i.e. not normal to the central axis X, as shown in FIGS. 2B and 2C, only a portion of the tilting plate abuts the edge 191. When the tilting plate 151 is set to tilt, the degree to which each steering cable extends or retracts depends on the distance between the point of attachment 126a, 127a of said cable to the tilting plate and the one or more portions of the tilting plate that abut the circumferential edge 181 or 191. In the embodiment of FIGS. 1A-1D, the circumferential edge 181 is flat circular, so that rotation of the ring 153 may result in a change in tilt of the tilting plate 151 and a small but nonetheless noticeable change in degree of bending of the tip 130. The extent to which the degree of bending of the tip changes during adjustment of the bending plane of the tip may be reduced by increasing the number of steering cables, e.g. by using 6, 8 or 10 steering cables instead of four.

It is however desirable to keep the total number of steering cables low, e.g. to 3 or 4, in particular when the steering cables extend through the flexible tubing 120 from the proximal end 122 thereof to the flexible tip 130. In the embodiment shown in FIGS. 2A-2C bending of the tip resulting from rotation of the user operable control is substantially compensated for by providing the circumferential edge 191 with a number of crests 192-195 which extend substantially parallel to the central axis X towards the first end of the handle, wherein between each of the crests the circumferential surface comprises a valley 196-199 which extends a shorter distance along the central axis towards the first end of the handle than the crests. The number of valleys corresponds to the number of steering cables and in the embodiment shown equals four. Each valley 196-199 is arranged along the circumference 191 at a position corresponding to a point of attachment 126a, 127a of a corresponding steering cable to the tilting plate. FIG. 2B shows crest 193 of the edge 191 contacting the tilting plate at a portion of the circumference of the titling plate that lies between two points of attachment of steering cables. If the user operable control 140 were rotated around the central axis X such that the point of attachment 127a of steering cable 127 to the steering plate would be closer to the proximal end of the handle, then a portion would abut the circumferential edge 191 at valley 197 instead. FIG. 2C shows the abutment section 190 with the tilting plate 151 in a different orientation in which the point of attachment 127a lies closer to the proximal end of the handle and the tilting ring is partially arranged in the valley 197.

FIG. 3 shows a cross-sectional view of a second embodiment of the medical device of the invention. In FIG. 3 the user operable control of the medical device 200 has not been shown for reasons of clarity, though the device is provided with a user operable control of a same construction as user operable control 140 shown in FIG. 1A. The medical device 200 comprises a handle 210 with a first end 211 and a second end 212, a tilting plate 251 tiltably supported on a spherical joint 252 and a ring 253 rotatably supported on the tilting plate and mechanically linked to the user operable control. The medical device 200 is similar to the medical device 100, but differs in that the spherical joint 252 is fixed to the support section rather than slidably supported on the support section. Though in this embodiment it is not possible to tension/relax the steering cables without changing the tilt of the tilting plate 251, otherwise the device functions in substantially the same manner as the medical device 100. That is, rotation of user operable control around the central axis X will result in a change in orientation of the bending plane of the tip 230 with respect to the distal end 221 of flexible tubing 220, and linear movement of the user operable control along the central axis X will result in a change in degree of bending of the tip in its bending plane, substantially without influencing the orientation of the bending plane.

Figure 4A:
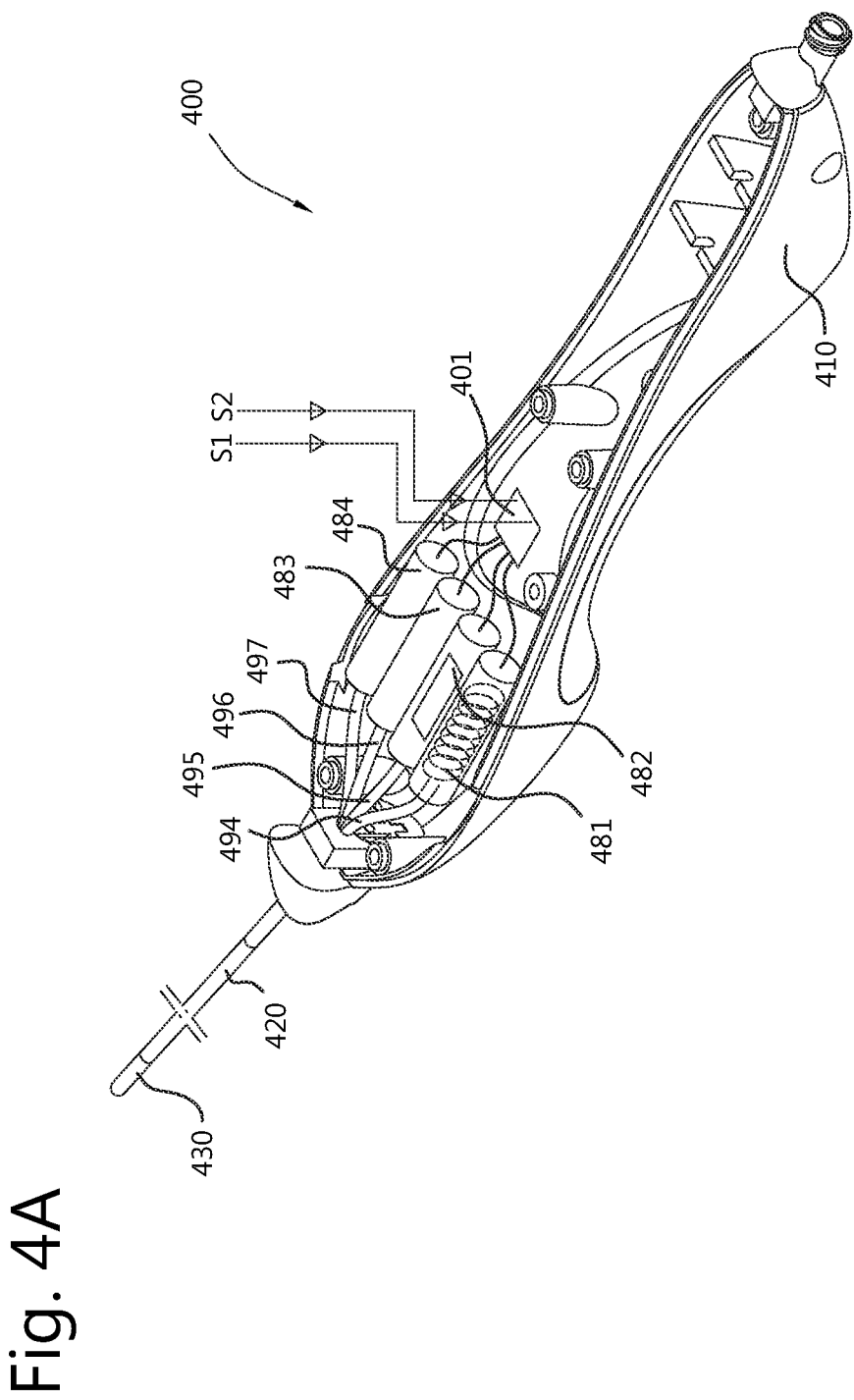
FIGS. 4A-4E illustrate various user operable controls of a medical device according to the present invention in which the tip is electronically actuated.

FIG. 4A shows the interior of a medical device 400 according to the present invention, provided with electromechanical actuators 481, 482, 483, 484 which together form a tip actuator assembly. Each of the electromechanical actuators is adapted for tensioning or relaxing a corresponding individual steering cable 494, 495, 496, 497 which extends through flexible tubing up to 420 the flexible tip 430, and is connected to a controller 401, which is adapted for providing control signals to the actuators based on a first signal S1 and a second signal S2. Each signals S1, S2 is indicative of the position and/or orientation of one or more user operable controls (not shown in FIG. 4A) with respect to the handle 410 of the medical device. The controller is adapted for controlling the actuators such that a change in signal S1 while signal S2 remains constant causes a change in bending plane of the tip 430 while maintaining the degree of bending of the tip constant, and such that a change in signal S2 while signal S1 remains constant causes a change in degree of bending of the tip in its bending plane while maintaining its bending plane constant.

Electromechanical actuators 481 and 482 are shown partially cut-away, with actuator 481 comprise an electromotor with a worm drive for tensioning and relaxing a corresponding steering wire, and actuator 482 comprising a piezoelectric element for the same purpose. Different kinds of electromechanical actuators for tensioning and relaxing a steering cable will be readily apparent to the skilled person.

Figure 4B:
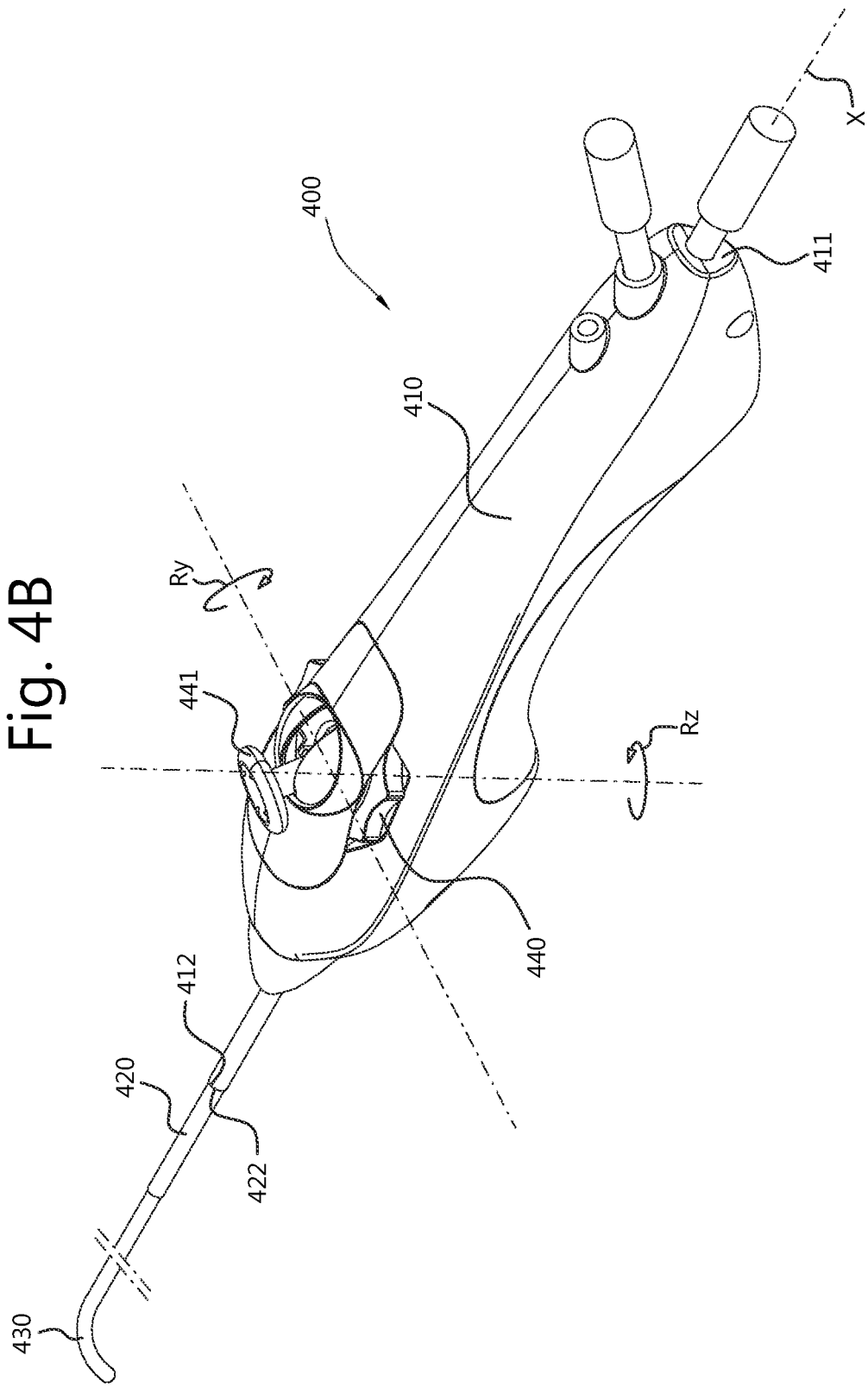

FIG. 4B shows the exterior of the medical device 400, comprising a first user operable control 440 that is supported on handle 410 between a first end 411 of the handle and an opposite end 412 thereof. The first user operable control 440 is rotatable, e.g. for one or more revolutions, around an axis of rotation Rz that is normal to the central axis X, and is connected to an electrical component, such as potentiometer, for generating the signal S1 as indicative of the orientation of the first user operable control 440 relative to the handle 410. The medical device 400 comprises a second user operable control 441 that is supported by the first user operable control, and rotates along with the first user operable control 440. The second user operable control further is moveable in a direction towards and away from the proximal end 422 of the flexible tubing 420 by rotating it around axis of rotation Ry that is normal to both the central axis X and the axis of rotation Rz. The second user operable control 441 is connected to an electrical component, such as a potentiometer, for generating the signal S2 indicative of the orientation of the second user operable control 441 relative to the first user operable control 440. Movement of the first user operable control relative to the handle 410 thus results in a change in the signal S1 that is received controller 401 and a corresponding adjustment of the bending plane of the tip 430, while movement of the second user operable control relative to the handle along a direction towards and away from the proximal end of the flexible tubing, results in a change in signal S2 that is received by the controller 401 and a corresponding adjustment of the degree of bending of the tip in its bending plane. The medical device 400 thus provides intuitive user controls for adjusting the orientation of the tip 430.

Figure 4C:
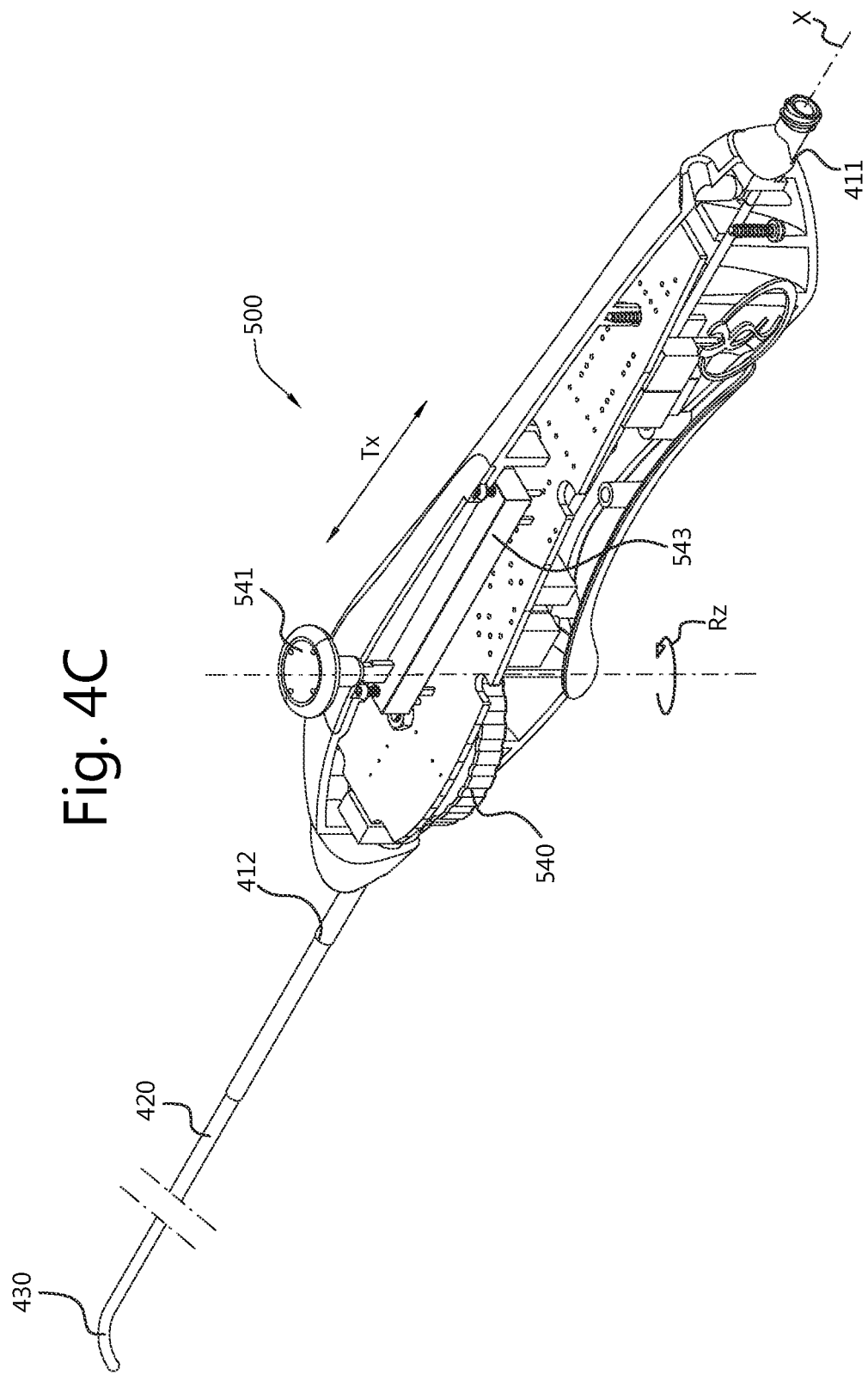

FIG. 4C shows a medical device 500 in which different first and second user operable controls are used than in the device 400, but which otherwise corresponds to the medical device 400, i.e. comprises a controller 401, electromechanical actuators 481-484 and so on. The device 500 is shown with a portion of the handle cut-away, so that the interior of the device can be seen more clearly. For controlling the bending plane of the tip 430, the device is provided with a first user operable control 540 in the form of a rotatable wheel 540. A portion of the wheel 540 extends out a slot through the handle, so that a user holding the device can rotate the wheel around its axis of rotation Rz, e.g. with his thumb and/or index finger. For controlling the degree of bending of the tip, the device is provided with a second user operable control 541 that is slidable in a direction Tx parallel to the central axis X to and away from the second end 412 of the housing. The second user operable control is attached to a slide-potentiometer 543, which is electrically connected to the controller 402.

Figure 4D:
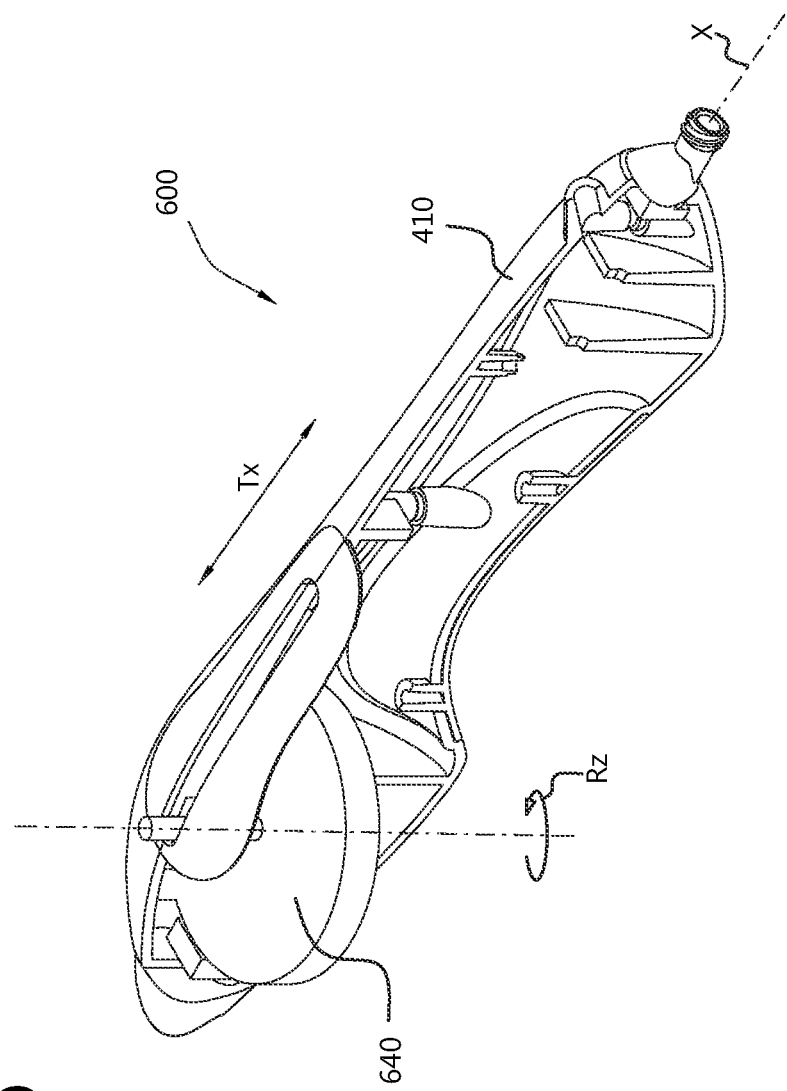

FIG. 4D shows a portion of a medical device 600, with the handle 410 shown partially cut-away and in which a single user operable control 640 is used instead of the first and second user operable controls of the device 400. The medical device 600 otherwise corresponds to the medical device 400, i.e. comprises a controller 401, electromechanical actuators 481-484 and so on. The single user operable control is formed as a dial 640 which is rotatable around its axis of rotation Rz for adjusting a bending plane of the tip, and which is also slidable along direction Tx for adjusting the degree of bending of the tip in its bending plane.

Figure 4E:
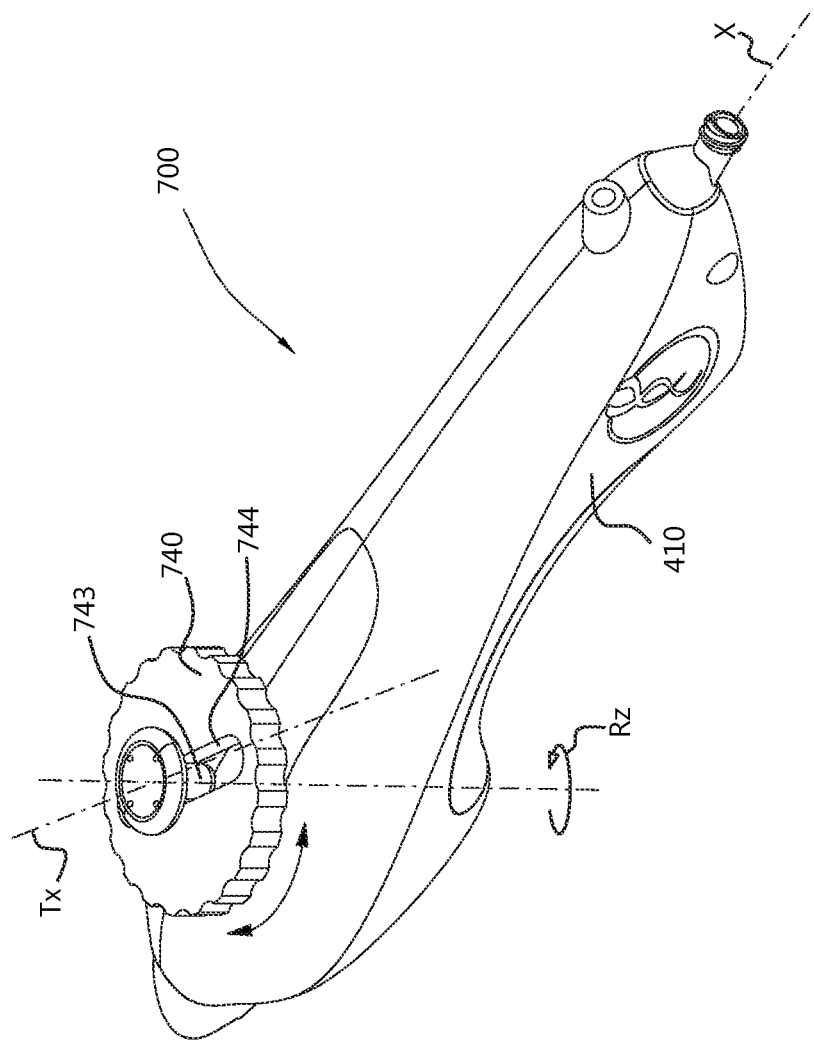

FIG. 4E shows a medical device 700, with a handle 410 and a first user operable control 740 in the form of a slotted control dial 740 which is rotatable around axis of rotation Rz, for adjusting a bending plane of the tip. In addition a second user operable control 743 is slidable within the slot 744 along direction Tx in which the slot 744 of the dial 740 extends, for adjusting the degree of bending of the tip in its bending plane.

FIG. 5 shows a third embodiment of the present invention. The medical device 800 comprises a first user operable control 840 and a tip actuator assembly which are of an identical or similar construction as the user operable control and tip actuator assembly of the device 100 of FIG. 1A. By moving the first user operable control 840 relative to the handle 810 of the device, the bending plane and degree of bending in said plane of first tip portion 830 relative to the distal end 821 of the flexible tubing 820 can be adjusted. The device is provided with an additional user operable control 841 and a corresponding tip actuator assembly, again of an identical or similar construction as the user operable control and tip actuator assembly of the device 100 of FIG. 1A. The additional user operable control 841 is adapted for adjusting the bending plane and degree of bending in said plane of second tip portion 833 relative to the distal end 831 of the tip portion 830.

Figure 6:
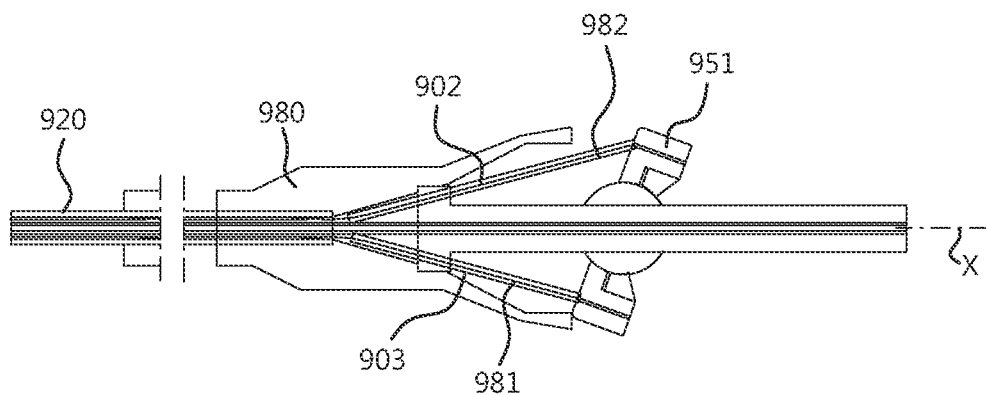
FIG. 6 shows a detail of an encapsulation as may be provided around one or more steering cables of any of the devices according to the present invention.

FIG. 6 shows a detail of a steering cables 981, 982 which each comprise a section which is surrounded by a flexible encapsulation 902, 903 that is attached at one end to the tilting plate 951 and extends to the proximal end 922 of the tubing 920, wherein the flexible encapsulation is adapted for allowing sliding movement of the section along the encapsulation while the encapsulation expands or contracts along the direction of sliding movement. Optionally, the flexible encapsulation extends within substantially the entire length of the tubing 920 to the flexible tip. The encapsulation substantially prevents buckling of the steering cables, e.g. when tension on a cable is reduced as is the case for cable 981. The flexible encapsulation is particularly advantageous in cases in which buckling of the steering cables would otherwise be likely to occur, e.g. in the device of FIG. 3, though the flexible encapsulation could be applied to the device of FIG. 1A as well, e.g. to reduce wear of the steering cables.

Figure 7A:
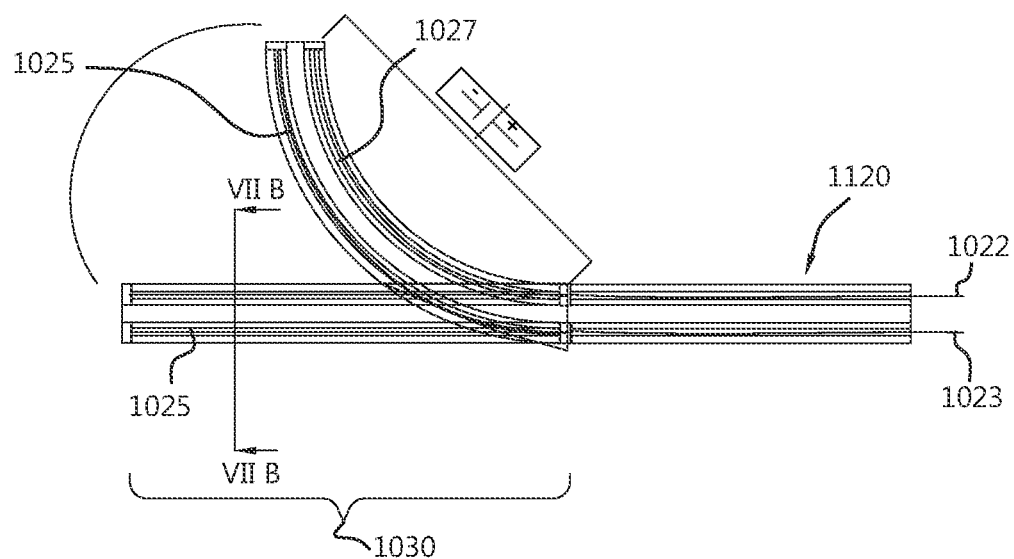
FIGS. 7A and 7B shows a detail of a flexible tubing having a flexible tip provided with electromechanical actuators which are electronically controlled through electrical conductors which extend through the tubing.
Figure 7B:
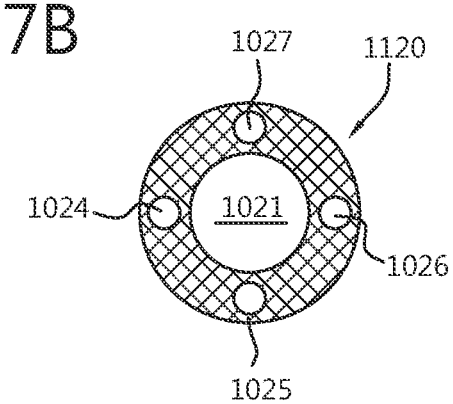

Instead of steering cables, the tips of the medical devices described herein may be controlled by means of electromechanical actuators arranged in or at the flexible tip and which are electrically connected to a controller within the handle which in turn is connected to the user operable control or controls. FIG. 7A shows a portion of a flexible tubing 1020 having a central channel for allowing passage of a fluid or element such as a guide wire or optical fiber to a flexible tip 1030. As can be seen in the cross-sectional view through line B-B of in FIG. 7B, within the tip 1030, the channel 1021 is surrounded by four electromechanical actuators in the form of memory shape wires 1024-1027 of a material which changes shape upon application of a voltage thereto. In the example, the wires 1024-1027 comprise or are made of nitinol which contracts when it is heated through passage of an electrical current thereto. Each of the wires 1024-1027 is connected at different ends thereof to corresponding electrical conductors 1022, 1023 for applying a potential difference to across the wires at the tip. Though in FIG. 7A only two such electrical conductors 1022, 1023 are shown which run through the length of the flexible tubing at least up to the tip, it will be understood that each of the electromechanical actuators is preferably connected to corresponding electrical conductors for supplying power to the actuator and/or applying a voltage across the actuator.

The present invention has been described above with reference to a number of exemplary embodiments as shown in the drawings. Modifications and alternative implementations of some parts or elements are possible, and are included in the scope of protection as defined in the appended claims.

The invention claimed is:

1. A medical device, comprising:
a handle with a central axis;
a flexible tubing which extends from the handle and has a proximal end fixed to the handle;
a flexible tip attached to a distal end of the flexible tubing and adapted for bending within multiple bending planes;
a tip actuator assembly for adjusting a bending plane of said multiple bending planes of the tip relative to the distal end of the flexible tubing and for adjusting a degree of bending of the tip in the bending plane; and
a user operable control, supported on the handle, and moveable in a first, rotational direction relative to the handle and to the tip actuator assembly around an axis of rotation, for causing the tip actuator assembly to adjust the bending plane of the tip substantially without rotating the flexible tubing,
wherein the user operable control further is slidable around the handle and the tip actuator assembly in a second, substantially linear direction towards and away from the proximal end of the flexible tubing, for causing the tip actuator assembly to adjust the degree of bending of the tip in the bending plane without adjusting the bending plane,
wherein the tip actuator assembly comprises:
a tilting plate which is tiltable relative to the central axis for adjusting the bending plane of the tip relative to the distal end of the flexible tubing and the degree of bending in said bending plane, the tilting plate being axially moveable along the central axis;
a blocking element that is fixed with respect to the central axis and configured to prevent rotation of the tilting plate around the central axis; and
multiple steering cables which are partially arranged within the flexible tubing and are connected at a first end to the tip and connected at a second end to the tilting plate.

2. The medical device according to claim 1, wherein the user operable control is mechanically connected to the tilting plate via a mechanical link mechanism which is adapted for converting movement of the user operable control in the first rotational direction to a tilt of the tilting plate for adjusting the bending plane of the tip, and for converting movement of the user operable control along the second direction to a movement of the tilting plate for adjusting the degree of bending of the tip in the bending plane.

3. The medical device according to claim 1, wherein the tilting plate has an annular edge, the linking mechanism comprising a ring in which the annular edge is accommodated such that the ring and tilting plate are rotatable relative to each other around a central axis of the ring while translation between the ring and tilting plate along said central axis of the ring is substantially blocked.

4. The medical device according to claim 3, wherein the annular edge of the ring is an outer annular edge of the ring and an outer surface of the ring comprises a first projection extending in a first plane parallel to the central axis of the handle, and adapted for sliding and rotating in a corresponding slot of the user operable control, so that rotational movement of the user operable control causes tilting of the tilting plate for adjusting the bending plane of the tip.

5. The medical device according to claim 4, wherein the outer surface of the ring comprises a second projection extending substantially parallel to the first projection and spaced apart from said first plane, and adapted for sliding and rotating in a corresponding slot of the user operable control, so that movement of the first user operable control along the second direction causes tilting of the tilting plate for adjusting the degree of bending of the tip in the bending plane.

6. The medical device according to claim 1, wherein the user operable control is moveable in the first, rotational direction relative to the handle and to the tip actuator assembly around an axis of rotation for causing the tip actuator assembly to adjust the bending plane of the tip without adjusting the degree of bending of the tip in said plane.

7. The medical device according to claim 1, wherein the handle comprises an abutment section with a circumferential edge arranged for abutment with at least a portion of a facing edge of the tilting plate, wherein the circumferential edge comprises a number of crests facing the tilting plate and a corresponding number of valleys between two neighbouring crests, wherein the number of valleys equals the number of steering cables, and wherein the valleys are arranged in line with the points of attachment of the steering cables to the tilting plate.

8. The medical device according to claim 1, wherein the multiple steering cables each comprise a section which is surrounded by a flexible encapsulation that extends from the proximal end of the tubing to the point of attachment of said steering cable within the handle, the flexible encapsulation being adapted for allowing sliding movement of the section along the encapsulation while the encapsulation expands or contracts along the direction of sliding movement.

9. The medical device according to claim 8, wherein the encapsulation comprises one or more of: a coil spring, an elastic sheathing, a bellows, and a braided tube.

10. The medical device according to claim 8, wherein the flexible encapsulation extends within substantially an entire length of the tubing to the tip.

11. The medical device according to claim 1, wherein the user operable control is provided with a locking mechanism for locking movement in the rotational direction of movement, and/or for locking movement along the second direction of movement.

* * * * *